United States Patent [19]

Otsuka et al.

[11] Patent Number: 5,190,750
[45] Date of Patent: Mar. 2, 1993

[54] METHODS FOR THE TREATMENT OF DEMYELINATING DISEASE, UVEITIS, OR GRAFT-VERSUS-HOST DISEASE USING TNF

[75] Inventors: Yoshiki Otsuka; Kazuyoshi Hori; Hiroshi Hayashi, all of Fuji, Japan

[73] Assignee: Asahi Kasei Kogyo Kabushiki Kaisha, Osaka, Japan

[21] Appl. No.: 665,876

[22] Filed: Mar. 7, 1991

[30] Foreign Application Priority Data

Mar. 9, 1990 [JP] Japan .................................. 2-56734
Mar. 9, 1990 [JP] Japan .................................. 2-56735
Mar. 9, 1990 [JP] Japan .................................. 2-56736

[51] Int. Cl.$^5$ .............................................. A61K 37/02
[52] U.S. Cl. ..................................... 424/85.1; 514/12; 514/21
[58] Field of Search ..................... 514/12, 21; 424/85.1

[56] References Cited

U.S. PATENT DOCUMENTS 4,963,354 10/1990 Shepard et al. ...................... 514/21

FOREIGN PATENT DOCUMENTS 0254647 1/1988 European Pat. Off. .
0261599 3/1988 European Pat. Off. .
0308378 3/1989 European Pat. Off. .
0325471 7/1989 European Pat. Off. .

OTHER PUBLICATIONS

Cancer Immunology Immunotherapy, 27, 103–108 (1989), Ehrke et al.
Chem-Abstracts, vol. 110, 1989, 13581e, Nakamura et al. (1989).
Piguet et al., J. Exp. Med. 166, 1280–1289 (1987).
Kulkarni et al. Exp. Eye Res. 46, 631–633 (1988).
Shalaby et al. Transplantation 47, 1057–1061 (1989).
Selmaj et al. The Journal of Imunpology 144 129–135 (1990).
Paya et al. International Immunology 2(9), 909–913 (1990).

Primary Examiner—Howard E. Schain
Attorney, Agent, or Firm—Pennie & Edmonds

[57] ABSTRACT

A pharmaceutical composition and a method for its use in the treatment of severe chronic inflammatory diseases, such as demyelinating disease, uveitis and graft-versus-host disease are provided. The composition comprises tumor necrosis factor as an active ingredient and at least one pharmaceutically acceptable carrier, diluent or excipient.

8 Claims, No Drawings

METHODS FOR THE TREATMENT OF DEMYELINATING DISEASE, UVEITIS, OR GRAFT-VERSUS-HOST DISEASE USING TNF

BACKGROUND OF THE INVENTION

1. Technical Field

This invention relates to a method for treating severe chronic inflammatory disease, such as demyeliniating diseases, uveitis, or graft-versus-host disease, by administrating tumor necrosis factor or "TNF" in an effective antisevere chronic inflammatory disease amount to a patient suffering from the disease.

2. Background Art

Severe chronic inflammatory disease is a generic name of a category of diseases which have no fundamental remedy because the mechanism of incidence has not been elucidated and is characterized by its regional and generalized chronic inflammatory symptoms. Severe chronic inflammatory disease consists of demyelinating disease, uveitis, graft-versus-host disease and the like.

The main morbific cause of demyelinating disease is a destruction of the myelin sheath of a nerve or nerves. It is generally classified into multiple sclerosis and acute disseminated encephalomyelitis. Demyelinating disease also includes disseminated sclerosis, leukodystrophy and the like. It has been considered that allergic reactions to the myelin sheath are related to the incidence of demyelinating disease. However, the cause of these reactions has not yet been elucidated. Multiple sclerosis is different from acute disseminated encephalomyelitis and other demyelinating diseases, because multiple sclerosis is characterized by remissions and persistently recurring exacerbations. Acute disseminated encephalomyelitis can be transformed into multiple sclerosis.

The presenting symptoms of demyelinating disease are neurologic disorders which mainly consist of ataxia and paresthesias. Demyelinating disease is sometimes fatal in the acute period. In spite of such severity, no efficient therapeutic method exists. As therapeutic methods for multiple sclerosis, adrenocortical hormone-like agents are used for the exacerbation period. For the remission period medical rehabilitation and medical preventive treatment against infection are utilized. But, demyelinating disease cannot be healed by these treatments. As therapeutic methods for acute disseminated encephalomyelitis, the use of adrenocortical hormone-like agents are effective in some cases. However, after the treatment, some problems remain such as neurologic disorders and transference into multiple sclerosis.

Uveitis is an inflammation of the eye which is caused by various diseases as an original disease, such as Behcet's disease, Vogt-Koyanagi-Harada syndrome, sarcoidosis or toxoplasmosis. The symptoms of anterior uveitis are iridocyclitis and hypopyon. The symptoms of posterior uveitis are opacity of the vitreousbody, hemorrhage and extravasation on the eyegnound, edema and opacification on the retina and neuritis optica. Posterior uveitis leads to a reduction or a loss of visual activity through complicated cataract or glaucoma. The mechanism of incidence of uveitis and the relation to the original diseases have not been elucidated. Neither have the cause or causes of Behcet's disease, Vogt-Koyanagi-Harada syndrome, sarcoidosis or toxoplasmosis been elucidated.

As therapeutic methods for uveitis, the instillation of mydriatic agents and steroidal agents and the general administration of steroidal agents have been conventionally utilized. The use of steroidal agents and immunosuppressive agents for a long-term administration has been utilized with the aim of prophylaxis and mitigation of uveitis, because uveitis is often recurs and tends to be chronic. However, steroidal agents and immunosuppressive agents such as cyclosporine are known for their strong side effects, and it is known that long-term administration can be life-threatening. Moreover, the effects of these agents have not been justified. The reduction in the dose and the interruption of the administration in cases where there is no improvement often causes the disease to become chronic.

Graft-versus-host disease (hereinafter "GVHD") is often observed in patients with foreign bone marrow transplantations. The major symptoms are fever, lesion, diarrhea and liver disorders. GVHD is a life-threatening disease. The bone marrow transplantation is performed on patients who are deficient in or lack hematopoietic stem cells and immunity-charging cells in cases such as aplastic anemia, severe immune difficiency and leukemia. It is also performed on patients whose myelopoietic function has been destroyed by radiation therapy and chemotherapy. However, there are many problems to be solved in the use of bone marrow transplantation, including the occurrence of such disorders as GVHD, interstitial pneumonia, reoccurrence and infection. GVHD sometimes causes interstitial pneumonia. The ratio of incidence of GVHD is very high when the bone marrow transplantation is utilized, making GVHD one of the major obstacles to bone marrow transplantation.

GVHD is classified into acute GVHD and chronic GVHD depending on the onset of GVHD. Also, there are differences between acute GVHD and chronic GVHD in clinical aspects. Acute GVHD occurs within 100 days after grafting. The main targets of acute GVHD are the skin, the liver and the gastrointestinal tract. The clinical symptoms of acute GVHD are erythema, bulla and erosion on the skin, icterus and diarrhea which are caused by the disorders of the organs mentioned above. Chronic GVHD occurs after 100 days following grafting. The targets of chronic GVHD are wider than those of acute GVHD. Therefore, the symptoms of chronic GVHD take various forms. Chronic GVHD is classified into localized GVHD and generalized GVHD according to the clinical findings. The main symptom of localized GVHD are lesions which include drying, lichen planus-like change, pigmentation, depigmentation and erythema accompanied with detachment. It sometimes accompanies with liver disorders. The syndrome of generalized GVHD consists of affections of the mucous membrane of the salivary gland, the mouth and the esophagus, the iachrymals, the lung, the bronchus, muscle and the joint. These symptoms lead to a reversion of autoantibodies and are similar to the symptoms of autoimmune disease.

As therapeutic methods for GVHD, general administration of immunosuppressive agents, such as methotrexate, steroids, azathioprine and cyclosporine A has been conventionally utilized. However, they have problems with side effects which have yet to be solved.

Tumor necrosis factor, or "TNF", was discovered originally in mouse serum after intravenous injection of bacterial endotoxin into mice primed with viable *Mycobacterium bovis*, strain Bacillus Calmette-Guerin (BCG). See, *Proc. Nat. Acad. Sci. U.S.A.*, 72(9), 3666–70 (1975).

TNF-containing serum from mice is cytotoxic or cytostatic to a number of mouse and human transformed cell lines, but less so to normal cells in vitro. It causes necrosis of transplantable tumors in mice. TNF also occurs in the sera of the rat, rabbit and guinea pig. Further, it is also known that TNF can be produced by mononuclear phagocytes, fibroblasts, B-cells, and the like derived from a mammal under certain conditions. In this connection, there are many reports in the literature which have been summarized by Lloyd J. Old in *Scientific American*, 258(5), 59-75 May, 1988).

TNF is now being developed under clinical trials for use as an anti-tumor agent. It is also reported that TNF has an anti-inflammatory effect and an anodzne effect [Japanese Patent Application laid-open No. 62-292727]. It is also reported that TNF has a suppressive effect against autoimmune disease defined as immune complex-disease [European Patent 254647] and a therapeutic effect against inflammatory skin disease such as atopic dermatitis [WO 90/05532]. However, there is no disclosure that TNF is effective against severe chronic inflammatory disease, such as demyelinating disease, uveitis, or graft-versus-host disease. On the contrary, it is reported that TNF may be one of the substances related to the destruction of the myelin sheath in demyelinating disease [Hofman et al., J. Exp. Med. 170, 607-612 (1989)]. It is also reported that an intravitreous administration of TNF causes an inflammatory reaction in the anterior eye [Rosembaum et al., Am. J. Pathol. 133. 47-53 (1988)]. It is also reported that TNF may be one of the substances related to skin and gastrointestinal tract disorders in acute GVHD [Piguet et al., J. Exp. Med. 166, 1280-1289 (1987)].

Considering the description of the above-mentioned reports, it was expected that TNF would not be useful for the purpose of treating demyelinating disease, uveitis, or graft-versus-host disease.

However, unexpectedly, our experimental data, i.e. in vivo data and data on the different condition of the dosage from those in the above-mentioned reports, show that TNF would be useful for the purpose of treating demyelinating disease, uveitis, or graft-versus-host disease.

Based on these novel findings, the present invention has been completed.

Accordingly, it is an object of the present invention to provide a novel therapeutic method effective for treating demyelinating disease.

Another object is to provide a novel therapeutic method effective for treating uveitis.

Another object is to provide a novel therapeutic method effective for treating graft-versus-host disease.

These and other objects of the invention as well as the advantages thereof can be had by reference to the following description and claims.

SUMMARY OF THE INVENTION

The foregoing objects are achieved according to the present invention by the inventors, discovery of a new type of pharmaceutical composition and method for its use in the treatment of demyelinating disease, uveitis or graft-versus-host disease, which are free from the above-mentioned drawbacks inevitably accompanying the conventional therapeutic compositions and methods. More particularly, it has been found that when tumor necrosis factor or "TNF" is administered to animal models of demyelinating disease, uveitis or graft-versus-host disease, the symptoms of the disease are suppressed. These results are based on a new type of activity of TNF different from any known activities mentioned above.

According to the present invention, a new method for treating demyelinating disease is provided which comprises administrating an effective anti-demyelinating disease amount of TNF to a patient having demyelinating disease. A new pharmaceutical composition for the treatment of demyelinating disease comprises TNF and at least one pharmaceutically acceptable carrier, diluent or excipient.

A new method for treating uveitis is also provided which comprises administrating an effective anti-uveitic amount of TNF to a patient having uveitis. A new pharmaceutical composition for the treatment of uveitis comprises TNF and at least one pharmaceutically acceptable carrier, diluent or excipient.

A new method for treating graft-versus-host disease is also provided which comprises administrating an effective anti-graft-versus-host disease amount of TNF to a patient having graft-versus-host disease. A new pharmaceutical composition for the treatment of graft-versus-host disease comprises TNF and at least one pharmaceutically acceptable carrier, diluent or excipient.

In the present invention, TNF obtained from serum or cells derived from a mammal can be used as an active ingredient. However, for purposes of utilizing the present invention on human patients, it is preferred to use pharmaceutical compositions containing human TNF from the standpoint of immunological compatibility.

Human TNF suitable for use in the present invention can be produced by recombinant DNA techniques. Alternatively, human TNF can also be produced by culturing cells derived from humans.

Suitable methods for producing human TNF by recombinant DNA techniques are described, for example, in Shirai T. et al., *Nature*, 313, 803-6 (1985) and Japanese Patent Application Laid-Open Specification No. 60-252496 (corresponds to European Patent Application Publication No. 0 158 286). By way of illustration, human TNF can be obtained by culturing *E. coli* to homogeneity.

The activity of human TNF during purification is monitored by mouse L-cell killing activity using a modification of the method of Williamson et al. employing L-M cells (American Type Culture Collection, CCL 1.2). See, Moss B., *Proc. Nat. Acad. Sci. U.S.A.*, 80, 5397-401 (1983). The number of surviving cells is determined by the photometric method of Ruff and Gifford, published in *J. Immun.*, 125, 1671-7 (1980).

The human TNF can also be produced by other known methods, including these described in Diane Pennica et al., *Nature*, 312, 20-7 (December, 1984); EP-A-168214; EP-A-155549; and the like.

The number of amino acid units constituting human TNF varies depending upon the production method used to obtain the TNF. For example, human TNF produced by recombinant DNA techniques described in EP-A-0158286 consists of 155 amino acid, units whereas human TNF produced by the method of Pennica et al., supra, consists of 157 amino acid units in the same sequence as in the TNF having 155 amino acid units and in addition having attached to its N-terminus, 2 amino acids.

The human TNF produced by recombinant DNA technique also includes a polypeptide having a methionine moiety attached to the N-terminus of the above-mentioned amino acid sequence and an intermediate having a partial or entire signal peptide for human TNF attached to the N-terminus of the above-mentioned amino acid sequence. It is possible to change a portion of the structure of a DNA coding for a polypeptide by natural or artificial mutation without significant change in the activity of the polypeptide.

The human TNF which can be used in the present invention includes a polypeptide having a structure corresponding to homologous variant(s) of the polypeptide having the above-mentioned amino acid sequence. Examples of homologous variants include polypeptides described in U.S. Pat. Nos. 4,677,063 and 4,677,064, the disclosures in which are incorporated herein by reference. All such physiologically active polypeptides are also hereinafter referred to as "human TNF".

Natural human TNF is likely to undergo biochemical modification or chemical modification, and is also likely to aggregate to form a multimer, such as a dimer or a trimer. These TNF polypeptides produced in nature are also hereinafter referred to as "human TNF", and can be used as an active ingredient in the pharmaceutical compositions of the present invention.

The pharmaceutical compositions of the present invention can be formulated into various preparations adapted, for example, to intravenous, intramuscular, subcutaneous, and intradermal injection, oral or rectal administration, external application and instillation. It is advantageous that the preparations are adapted for the administration of a polypeptide composition.

In preparing the pharmaceutical compositions of the present invention, various additives can be included as may be appropriate, such as one or more carriers, diluents, excipients, fluidizing agents, binding agents, stabilizers, thickeners, pH adjusting agents and the like.

Suitable carriers, diluents and excipients include starches and derivatives thereof, such as potato starch, corn starch, dextrin and wheat starch and hydrxypropyl starch; sugars, such as lactose, glucose, sucrose, mannitol and sorbitol; celluloses, such as methylcellulose, carboxylmethylcellulose and hydroxypropylcellulose; inorganic compounds, such as sodium chloride, boric acid, calcium sulfate, calcium phosphate and precipitated calcium carbonate; and the like.

Suitable fluidizing agents include magnesium oxide, synthetic aluminum silicate, metasilicic acid, magnesium aluminum oxide, hydrous silicic acid, anhydrous silicic acid, talc, magnesium stearate, kaolin and the like.

Suitable binding agents include polyethylene glycol, polyvinyl pyrrolidone, polyvinyl alcohol, gum arabic, tragacanth, sodium alginate, gelatin, gluten, and the like.

Suitable stabilizers include proteins, such as albumin, protamine, gelatin and globulin; amino acids and salts thereof, and the like.

Suitable pH adjusting agents include hydrochloric acid, sodium hydroxide, phosphates, citrates, carbonates, and the like.

The pharmaceutical compositions of the present invention can be administered to a patient in an amount such that the daily dose of TNF for an adult is generally in the range of from about 50 to 100,000,000 units, and preferably from about 50 to 500,000 units in the case of local administration, from about 1,000 to 10,000,000 units in the case of general injection such as intravenous injection and intramuscular injection, and from about 10,000 to 100,000,000 units in the case of oral administration.

The term "unit" as used above means a quantity of TNF by which 50% of $1 \times 10^5$ cells/ml of L-M cells (American Type Culture Collection CCL 1.2) are killed. This quantity is measured as follows: As culture vessels, there are employed 96-well microtiter plates produced by Flow Laboratories, Inc. (U.S.A.). L-M cells are cultured in Eagle's minimum essential medium containing 1 v/v % of fetal calf serum [the composition of this medium is described, for example, in Tissue Culture, edited by Junnosuke Nakai et al., Asakura Shoten, Japan (1967)]. A sample (0.1 ml), serially diluted with the medium, and the L-M cell suspension (0.1 ml, $1 \times 10^5$ cells/ml) are mixed into each well of the plates and the plates are incubated at 37° C. for 48 hours in air containing 5% carbon dioxide. At the end of the culture period, 20 µl of glutaraldehyde is added to fix the cells. After fixation, the plates are washed with distilled water and allowed to dry, and 0.05% methylene blue (0.1 ml) is added to stain the viable cells. The plates are thoroughly washed with distilled water to remove excess dye and allowed to dry. Hydrochloric acid (0.36N) is added to each well to extract the dye from stained cells. Absorbance of each well at 665 nm is measured with Titertek Multiskan produced by Flow Laboratories, Inc. (U.S.A.). The absorbance is proportional to the number of viable cells. The above-mentioned quantity of the physiologically active polypeptide of the present invention by which 50% of $1 \times 10^5$ cells/ml of L-M are killed is obtained by a plotting of the dilution versus the absorbance.

The dosage regimen for treating a patient with the pharmaceutical composition of the present invention varies according to the age and symptoms of the patient. As mentioned above, the composition can generally be administered over several days to several weeks in a daily dose of 50 to $10^8$ units. The daily dose can be administered to a patient all at once or in several applications. The administration of the present pharmaceutical composition can be conducted each day, or alternatively, the administration can be conducted at intervals. Representative examples of the dosage regimen are as follows:

(a) daily administration for 1 to 4 weeks;
(b) daily administration for 1 to 6 days, alternatively with a pause for one day to several weeks;
(c) administration for one day per week; and
(d) daily administration for 5 days, alternately with a pause of one month.

DESCRIPTION OF PREFERRED EMBODIMENTS

EXAMPLE 1

Experimental allergic encephalomyelitis(EAE) has been studied for many years as an animal model for demyelinating disease [Tahira et al., Experimental Allergic Encephalomyelitis(EAE). [Multiple Sclerosis -basic and clinical-] Shiokoigakushuppansha 241 (1985)]. A quantity (0.1 ml) of emulsion of bovine myelin basic protein and Freund's complete adjuvant is subcutaneously injected to the footpad of a 5 week-old female Hartley guinea pig to induce EAE. After the injection, 300,000 units/guinea pig of human TNF obtained by the recombinant technique according to the method described in European Patent Application Publication No. 0 158 286 is intraperitoneally injected to the each of 8 guinea pigs every day until day 12. 0.1% gelatin containing-phosphate buffer solution which is used to dilute human TNF is injected to the each of 8 guinea pigs in a control group by the same schedule and method as those in the TNF-injection group. The neurological signs are observed and recorded every day to determine the onset of the disease. And findings are confirmed by the histologic examination of the brain and the spinal cord 21 days after the injection.

The observation period is set for 21 days after the injection. The number of guinea pigs which show severe clinical signs during the recorded period is statistically compared. As shown in Table 1, statistically significant suppression of EAE incidence based on Wilcoxon's rank sumtest is observed in the TNF-injection group. Moreover, 2 out of 8 guinea pigs in the control group die by acute encephalomyelitis. By contrast, there is no guinea pig dead in the TNF-injection group.

TABLE 1

| | No. scored/No. tested | | | | |
|---|---|---|---|---|---|
| | − | + | ++ | +++ | ++++ |
| CONTROL | | | 2/8 | 2/8 | 2/8 |
| TNF | | | 0/8 | 2/8 | 0/8 |

The difference between the control group and the TNF-injected group is significant by Wilcoxon's rank sum test (p<0.05).

Individual animals are scored as follows;
−: normal
+: weakness of limbs
++: ataxia
+++: paralysis, tremor
++++: death These results indicate the suppressive effect of TNF against demyelinating disease.

EXAMPLE 2

Endotoxine-induced rabbit uveitis is examined as an animal model for anterior uveitis according to a general method by Rosenbaum et al., [Am. J. Pathol. 133, 47–53 (1988)]. New Zealand white female rabbits are anesthetized intramuscularly with a combination of ketamine(30 mg/kg) and xylazine(5 mg/ml). A quantity (1 ng) of Escherichia coli endotoxin is injected by a 30-gauge needle into the vitreous body to induce anterior uveitis. Incidence of the disease is determined by the histologic examination of paraffin embedded sections of the bulbus oculi, leakage protein quantification in aqueous humor and extravasated cell numbers in aqueous humor, when the rabbits are killed 24 hours after the injection. Protein is quantitated according to the binding of brilliant blue as described by Bradford. Cell numbers are counted with a hemocytometer. 24 hours and 1 hour before the injection, 300,000 units/kg of human TNF obtained by the method described in Example 1 is intravenously injected via the ear vein of each of 4 rabbits. A 0.1% gelatin containing-phosphate buffer solution which is used to dilute human TNF is injected to each of 4 rabbits in the control group by the same schedule and method as those in the TNF-injection group.

According to the histological examination, infiltration of many monocytes and neutrophils in the iris and the ciliary epithelium is observed in the control group. By contrast, TNF treatment results in a significantly decreased number of infiltrated cells. As shown in Table 2, the amount of leakage protein and the number of extravasated cells in aqueous humor as an index of anterior inflammation in the TNF-injection group are decreased compared to those of the control group.

TABLE 2

| | Protein (mg/ml) | Cell ($\times 10^6$/ml) |
|---|---|---|
| TNF | 14.9 ± 5.8 | 1.52 ± 0.63 |
| CONTROL | 2.0 ± 1.1 | 0.21 ± 0.14 |

N = 4 for each group.

Average are expressed as mean ± standard error.

These results indicate the suppressive effect of TNF against endotoxine-induced uveitis.

EXAMPLE 3

Rat experimental autoimmune uveoretinitis(EAU) is examined as an animal model for uveitis including posterior uveitis according to a general method by Nussenblatt et al., [Arch. Ophtaimol, 100, 1146–1149 (1982)]. A quantity (0.05) ml of mixed emulsion with bovine S-antigen(20 μg/rat) prepared by Dorey et al., [Ophthalmic res. 14, 249 (1982)] and Freund's complete adjuvant is administrated to a female Lewis rat (5 week-old) by the rear-footpad route to induce EAU. Incidence of the disease is determined by the histologic examination of paraffin embedded sections of the bulbus oculi, when the rats are killed 14 days after the administration. A quantity (100,000 units/kg) of human TNF obtained by the method described in Example 1 is intraperitoneally injected into the each of 4 rats every day after the S-antigen administration until day 14. A 0.1% gelatin containing-phosphate buffer solution which is used to dilute human TNF is injected to the each of 4 rats in the control group by the same schedule and method as those in the TNF-injection group.

According to histologic examination, infiltration of many monocytes and neutrophils in the whole area of the retina and the choroid is observed in the control group. By contrast, TNF treatment results in a significantly decreased number of infiltrated cells.

The results in Examples 2 and 3 indicate the suppressive effect of TNF against uveitis.

EXAMPLE 4

Mouse acute GVHD is examined as an animal model for GVHD according to a method by Piguet et al. [J. Exp. Med. 166, 1280–1289 (1987)]. A 3 month-old F1 mouse(B10×CBA) is irradiated(800 rad) and intravenously injected from tail vein with $2 \times 10^6$ lymphocytes prepared from the inguinal and axiliary lymph nodes of C57BL/10 mice and $2 \times 10^6$ bone marrow cells derived from C57BL/10 mice from which T lymphocytes are depleted by using anti-Thy1-antibodies and complements. After the irradiation, the mice are housed with neomycin(0.5 mg/ml)-containing water. After the next day of the transplantation 10,000 units/mouse of human TNF obtained by the method described in Example 1 is intravenously injected every two days until day 41. A quantity of 0.1% gelatin containing-phosphate buffer solution which is used for diluting human TNF is injected to each of 4 mice in the control group by the same schedule and method as those in the TNF-injection group. Incidence of the disease is determined by the number of mice surviving 84 days after the transplantation, and histologic examination of the skin and the duodenum 21 days after the transplantation.

According to the survival ratio as shown in Table 3, a dead mouse is observed 21 days after the transplantation in the control group. The death ratio is increased after day 21 and all mice are dead 12 weeks after the transplantation. By contrast, in the TNF-injection group, no mouse is dead during the injection period and only 2 out of 8 mice are dead even 12 weeks after the transplantation.

According to the histological examination, in the control group, flattening of villi, cellular necrosis in crypts and lymphocyte infiltration into the submucosa are observed in addition to epidermal thickening, cellular infiltration and necrosis of epidermal cells. In the TNF-injection group, such changes are supressed.

TABLE 3

| | Survival Ratio Day After Transplantation | | | |
|---|---|---|---|---|
| | 21 day | 42 day | 63 day | 84 day |
| CONTROL | ↓ | ↓ | ↓ | 0/8 |
| TNF | 8/8 | 8/8 | ↓ | 6/8 |

These results indicate the suppressive effect of TNF against GVHD.

EXAMPLE 5

Human TNF is produced by recombinant DNA technique by the method described in Example 1. Using the thus-produced recombinant human TNF, a lyophilized preparation for injection having the following composition is formulated.

| Formulation | |
|---|---|
| Human TNF | $5 \times 10^5$ units |
| D-Mannitol | 30 mg |
| Normal serum albumin (human) | 10 mg |
| Sodium chloride | 2.0 mg |
| Sodium dihydrogen phosphate dihydrate (adjusted at pH 8.0 by sodium hydroxide) | 3.9 mg |

The foregoing description is intended to illustrate the invention, and it is understood that changes and variations can be made in the foregoing embodiments without departing from the spirit and scope of the invention which is defined in the following claims.

We claim:

1. A method for treating demyelinating disease, comprising administering a pharmaceutical composition, consisting essentially of an effective anti-demyelinating disease amount of tumor necrosis factor and at least one pharmaceutically acceptable carrier, diluent or excipient, to a patient having demyelinating disease.

2. A method for treating uveitis, comprising administering a pharmaceutical composition, consisting essentially of an effective anti-uveitic amount of tumor necrosis factor and at least one pharmaceutically acceptable carrier, diluent or excipient, to a patient having uveitis.

3. A method for treating graft-versus-host disease, comprising administering a pharmaceutical composition, consisting essentially of an effective anti-graft-versus-host disease amount of tumor necrosis factor and at least one pharmaceutically acceptable carrier, diluent or excipient, to a patient having graft-versus-host disease.

4. The method according to claim 1, wherein the demyelinating disease is multiple sclerosis.

5. The method according to claim 1, wherein the demyelinating disease is acute disseminated encephalomyelitis.

6. The method according to any one of claims 1, 2, or 3, wherein the tumor necrosis factor is produced from a human-derived cell.

7. The method according to any one of claims 1, 2, or 3, wherein the tumor necrosis factor is produced by means of recombinant DNA technique.

8. The method according to any one of claims 1, 2, or 3, wherein the tumor necrosis factor is adapted for intravenous, intramuscular, subcutaneous, or intradermal injection, oral or rectal administration, external application or instillation.

* * * * *